US006321105B1

United States Patent
Jenkins et al.

(10) Patent No.: US 6,321,105 B1
(45) Date of Patent: Nov. 20, 2001

(54) METHOD FOR DIAGNOSING NEUROLOGICAL, NEURODEGENERATIVE AND PSYCHIATRIC DISEASES BY MAGNETIC RESONANCE IMAGING USING CONTRAST AGENTS WITH HIGH MAGNETIC SUSCEPTIBILITY AND EXTENDED PLASMA HALF LIFE

(75) Inventors: Bruce G. Jenkins, Belmont; Joe B. Mandeville, Somerville, both of MA (US); Friedrich M. Cavagna, Scanzorosciate (IT)

(73) Assignee: Bracco S.p.A., Milan (IT)

( * ) Notice: Subject to any disclaimer, the term of this patent is extended or adjusted under 35 U.S.C. 154(b) by 0 days.

(21) Appl. No.: 09/287,268

(22) Filed: Apr. 7, 1999

Related U.S. Application Data
(60) Provisional application No. 60/081,048, filed on Apr. 8, 1998.

(51) Int. Cl.[7] .................................................... A61B 5/05
(52) U.S. Cl. .................... 600/407; 600/420; 324/307; 324/309; 324/312; 424/9
(58) Field of Search ........................... 600/420, 407; 324/307, 309, 312; 424/9

(56) References Cited

U.S. PATENT DOCUMENTS

| | | | |
|---|---|---|---|
| 5,352,979 | * 10/1994 | Conturo | 324/307 |
| 5,357,959 | * 10/1994 | Fishman | 128/653.2 |
| 5,376,667 | * 12/1994 | Somers et al. | 514/304 |
| 5,459,400 | * 10/1995 | Moonen | 324/309 |
| 5,494,655 | *  2/1996 | Rocklage et al. | 424/9.36 |
| 5,685,305 | * 11/1997 | Moonen et al. | 324/306 |
| 5,833,947 | * 11/1998 | Rocklage et al. | 424/9.36 |
| 5,902,815 | *  5/1999 | Olney et al. | 514/285 |
| 5,914,097 | *  6/1999 | White | 424/9.365 |

OTHER PUBLICATIONS

Marota et al Proceedings of International Society for Magnetic Resonance in Medicine 5th Scientific 1997, vol. 2, p. 731 "Activation of Rat Brain by Cocaine: Functional Imaging with Bold etc." XP–00211551.

Cuenod et al Proceedings of Society of Magnetic Resonance in Medicine 12th Scientific vol. 3, 8/93 vol. 3, p. 1387 "Local Brain response etc." XP002110552.

Graham et al. Proceedings of Society of Magnetic Resonance in Medicine 2nd meeting Comparison of Gadolinium Con trast Bolus and Bold Assessments 8/94 vol. 1, p 276 XP002110553.

Silva et al Magnetic Resonance in Medicine, vol. 33, 1995, p. 209–214 "Multi–Slice MRI of Rat Brain Perfusion During Amphetamine Stimulation Using Arterial Spin Labeling" XP002110550.

(List continued on next page.)

Primary Examiner—Marvin M. Lateef
Assistant Examiner—Jeoyuh Lin
(74) Attorney, Agent, or Firm—Nixon & Vanderhye

(57) ABSTRACT

A method for Magnetic Resonance Imaging (MRI) of changes in neurotransmitter and neuroreceptor activity as a metabolic response to diagnostic challenge or therapeutic treatment in a patient with suspected or already diagnosed mental illnesses of psychiatric, neurodegnerative or neurological nature, by (a) administering to a patient a drug eliciting an MRI detectable hemodynamic response; (b) administering to the patient an MRI contrast agent with high magnetic susceptibility, and then (c) measuring, in a spatially and temporally resolved manner, relative Cerebral Blood Volume (rCBV) changes associated to neuronal activation using $T_2$- or $T_2^*$-weighted MRI scans at the equilibrium distribution of said contrast agent.

18 Claims, 7 Drawing Sheets

OTHER PUBLICATIONS

Jones et al NMR in Biomedicine vol. 10, 1997, p. 59–66 "A Study of the Contribution of Changes in the Cerebral Blood Volume to the Haemodynamic etc." XP002110549.

Mandeville et al Magnetic Resonance in Medicine, vol. 39, 4/98 p 615–624 "Dynamic Functional Imaging of Relative Cerebral etc." X002110548.

Ching et al Magnetic Resonance in Medicine, vol. 38, 1997, p. 389–398 "Detection of Dopaminergic Neurotransmitter Activity etc." XP002110546.

Burdett et al. Magnetic Resonance Imaging, vol. 13, No. 4, 1995, p. 549–533 "Visualisation of Changes in Regional Cerebral BlooD Flow etc." XP002110547.

* cited by examiner

METHOD FOR DIAGNOSING NEUROLOGICAL, NEURODEGENERATIVE AND PSYCHIATRIC DISEASES BY MAGNETIC RESONANCE IMAGING USING CONTRAST AGENTS WITH HIGH MAGNETIC SUSCEPTIBILITY AND EXTENDED PLASMA HALF LIFE

This application claims benefit of Provisional No. 60/081,048, filed Apr. 8, 1998.

BACKGROUND OF THE INVENTION

A large number of psychiatric (i.e. schizophrenia), neurological (i.e. Parkinson's disease), and neurodegenerative (i.e. Huntington's chorea) pathologies involve changes of mental states or conditions based upon changes in neurotransmitter and receptor balances. Detection of such changes may allow for diagnosis well ahead of manifestation of severe clinical symptoms, and knowledge of the nature and the extent of such changes is of paramount importance for the determination of therapy. For instance, in Parkinson's disease the chronic use of L-DOPA therapy leads to a progressive diminution in its efficacy. Thus, one would like to be able to monitor the progression of the disease more closely to effect possible changes in dosing. Similar problems present for many of the currently used dopaminergic ligands in schizophrenia. Determination of the effects of these therapies upon the brain is very difficult at the present time.

Two methodologies have been widely used for the determination of changes in neurotransmitter and receptor dynamics in vivo. These two techniques (Positron Emission Tomography and Single Photon Emission Computed Tomography, PET and SPECT) involve the use of radioactivity. Positron Emission Tomography is a very versatile technique which has been used successfully for the mapping of Cerebral Blood Flow (CBF), cerebral glucose metabolism (using $^{18}$F-fluorodeoxyglucose, FDG) or receptor activity (using radioactive pharmacological ligands), while SPECT is more limited to the detection of nonspecific processes. Unfortunately, both techniques suffer from severe limitations in spatial and temporal resolution, and cannot be proposed for repeated applications. Moreover, PET is characterized by limited availability and high costs, which are partly due to the short half-life of many of the radiopharmaceuticals which have to be administered.

A third alternative has recently been developed and is called pharmacological Magnetic Resonance Imaging (phMRI) and is based upon changes in Blood Oxygen Level Dependent (BOLD) contrast. The method rests on the spatially and temporally resolved visualization of the hemodynamic response evoked by neuronal activation following application of a specific pharmacological stimulus. Briefly: neuronal activation results in an increased local metabolic activity, increased oxygen consumption and increased local concentration of paramagnetic deoxyhemoglobin. Since the latter is compartmentalized in the vasculature, its higher magnetic susceptibility leads to a decreased Signal Intensity (SI) of brain tissue in $T_2^*$-weighted MR images. This effect is however quickly overcompensated by increased relative Cerebral Blood Flow (rCBF), with consequent inflow of fresh blood with lower content in deoxyhemoglobin, leading finally to increased SI on $T_2^*$-weighted images in the area of neuronal activation.

While phMRI offers the needed high spatial and temporal resolution as well as the non-invasiveness of MRI, it suffers from the lack of sensitivity of the BOLD effect, which amounts to an increase in SI of only 2–3% at clinical field strengths. This is by far not enough for the establishment of a robust clinical procedure. This problem has been dealt with, with better results, for the analogous technique called functional MRI (fMRI), which differs from phMRI by the nature of the stimulus which is sensorial or motor rather than pharmacological. In fMRI, the low intensity of the BOLD effect is compensated by repeated acquisition of alternating data blocks at rest and under stimulation and using statistical approaches like Multivariate Analysis of Covariance (ManCova) to generate Statistical Parameter Maps (SPM) which represent the statistical significance—on a pixel-by-pixel basis—of any differences in SI between scans taken at rest and during stimulation. However, this solution is not applicable to phMRI due to the long duration (typically 1 hour) of the response to pharmacological stimulation, as opposed to the short duration (seconds) to sensorial or motor stimulation.

While two reports have described the use of contrast agents to increase the sensitivity of phMRI (1, 2), none of them recognized, nor even suggested, the diagnostic potential of the technique and none of them tested its applicability on animal models of disease. On the contrary, the present application acknowledges the lack of methods to visualize brain disorders by imaging the underlying imbalances in neurotransmitters and neuroreceptors using specific pharmacological stimuli and non-invasive imaging techniques with high spatial resolution and gives a solution to said medical need.

SUMMARY OF THE INVENTION

In its most important aspect, the present invention is a method to detect, diagnose and stage neurological disorders by taking $T_2$- or $T_2^*$-weighted images of the brain after i.v. administration of a susceptibility contrast agent with extended half life (so-called negative blood-pool contrast agents). Baseline images are taken at the equilibrium distribution of the agent. For any given MR sequence and for any given concentration of a given agent in blood, a drop in SI of brain tissue will be observed which shows a positive correlation with relative Cerebral Blood Volume (rCBV). Appropriate mathematical treatment of the signal intensity loss yields $\Delta R_2$ or $\Delta R_2^*$ (depending on the use of $T_2$- or $T_2^*$-weighted sequences, respectively), which can be taken to be proportional to the changes in rCBV. Therefore, one can obtain rCBV maps from baseline scans after contrast administration.

The patient, human being or animal, is then subjected to a pharmacological diagnostic challenge by administration of a stress agent, the nature of which depends closely on the nature of the suspected disease (if a diagnosis is attempted) or of the already diagnosed disease (if choice of therapy or assessment of success of therapy are the aims of the procedure). Basically, all known neurotransmitters, their agonists and antagonists (at both the release and receptor level) can be administered as stress agents for diagnostic challenge.

The metabolic response associated with neuronal activation following diagnostic challenge results in a substantial increase in rCBV and hence a decrease in SI (or increase in $\Delta R_2$ and $\Delta R_2^*$) in the area of activation, thus allowing a mapping of neurotransmitter activity and specifically the detection of imbalances in neurotransmitter and receptor activity. In a preferred embodiment, this method can be used to assess the performance of therapeutic drugs by comparing the response to the stimulus in the naive patient to the response in the patient treated with various doses of the same drug or with different drugs, greatly facilitating the establishment of therapy which otherwise would have to rely solely on the observation of clinical symptoms, usually over an extended period of time.

Thus, our invention provides the capability to detect, diagnose and grade neurological, neurodegenerative and psychiatric disorders by monitoring rCBV changes following diagnostic challenge in $T_2$- or $T_2^*$-weighted MR images taken at the equilibrium distribution of a susceptibility contrast blood pool agent.

DESCRIPTION OF THE DRAWINGS

The file of this patent contains at least one drawing executed in color. Copies of this patent with color drawings will be proved by the Patent and Trademark Office upon request and receipt of the necessary fee.

DESCRIPTION OF THE INVENTION

Figure 1:
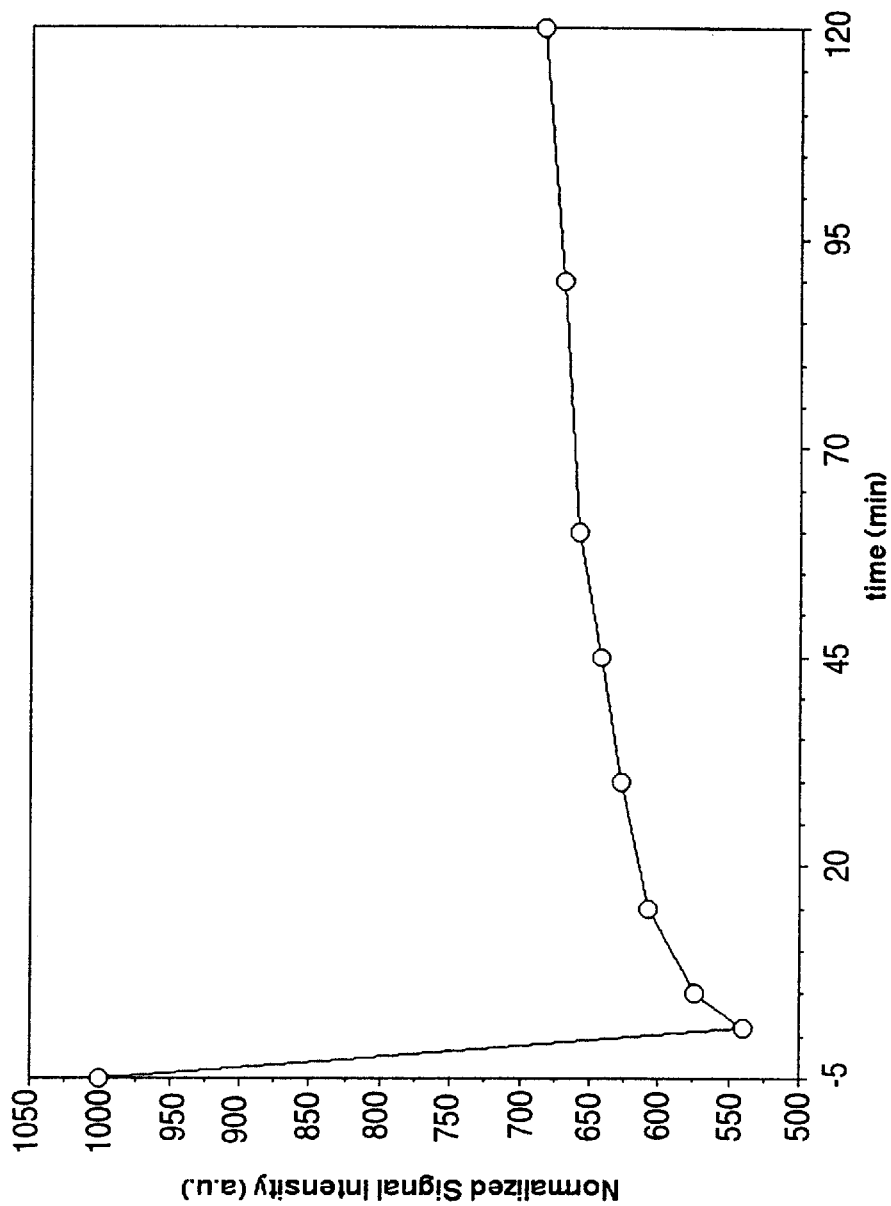
FIG. 1 is a normalized signal intensity time curve of rat brain after 60 μmol Fe/kg of the superparamagnetic contrast agent described in example 1a), at 2T using a gradient echo sequence (500 ms/30 ms /30°; TR/TE/α).

Disclosed is a method to diagnose neurological, neurodegenerative, psychiatric and other disorders by measuring in a spatially and temporally resolved manner rCBV changes associated to neuronal activation, following a diagnostic challenge, by using $T_2$- or $T_2^*$-weighted MRI scans at the equilibrium distribution of a susceptibility contrast agent with extended plasma half life.

In a preferred embodiment, the susceptibility contrast agent essentially comprises magnetic particles, meaning particles with ferromagnetic, antiferromagnetic or superparamagnetic properties. For example, such magnetic particles may include (a) a single magnetic crystal without any nonmagnetic material, or (b) a conglomerate of many magnetic crystals without any nonmagnetic material, or (c) a single magnetic crystal mixed with or bound to or coated with nonmagnetic material, usually synthetic or natural polymers or mixtures hereof, or (d) a conglomerate of many magnetic crystals bound to, coated with or mixed with nonmagnetic material as described in (c).

Contrast agents belonging to these categories have been described in the scientific and patent literature. For instance, two so called USPIO (Ultrasmall Superparamagnetic Iron Oxide) belonging into the category (b) are known as Sinerem® (3, 4, 5), being clinically tested by Guerbet, and as MION (Monocrystalline Iron Oxide Nanopolymer), respectively (6, 7, 8, 9). The coating material for both Sinerem® and MION is a dextran polymer. Other particles with larger magnetic core comprising multiple magnetic crystals have been described in the literature and are often called SPIO for Superparamagnetic Iron Oxide. Examples include Feridex® (10, 11, 12, 13) as presently available from Berlex in the US and from Guerbet in Europe, Resovist® as currently tested clinically by Schering (14, 15, 16, 17), and superparamagnetic blood pool agent as described by Bracco in U.S. Pat. No. 5,464,696, U.S. Pat. No. 5,587,199, and U.S. Pat. No. 5,545,395. The particles described above vary strongly with respect to their imaging properties. For instance, the $r_2/r_1$ ratio varies between low values for USPIO type agents (for instance 3.07 for Sineremo® as described by Berry (3)), or 1.72 as described by Fahlvik in WO 97/36617, or 3.54 for MION as described by (6), and values as high as 40 for SPIO agents like Bracco's.

While the $r_2/r_1$ ratio has a strong bearing in the ability of an agent to generate positive or negative contrast in the vasculature for any given concentration or MRI sequence, the ability to generate signal loss in brain tissue is largely dependent on the difference in bulk susceptibility between the blood and the extravascular space, which in turn depends strongly on the susceptibility rather than on the $r_2/r_1$ ratio of the contrast agent. Agents which are likely to work best are therefore those with the highest magnetic susceptibility as for instance the agent described in U.S. Pat. No. 5,464,696 with mass magnetic susceptibility of 43,663×$10^{-6}$ cgs. Thus, it is a distinct feature of our invention that it will work with agents covering the whole range of $r_2/r_1$ ratio values.

In a second preferred embodiment, the susceptibility contrast agent comprises magnetic particles with extended plasma half life, i.e. it is a ferromagnetic or antiferromagnetic or superparamagnetic blood pool agent. This feature allows for repeated imaging at the equilibrium distribution of the agent after a single injection. Since the metabolic response to a diagnostic challenge (neuronal activation with ensuing hemodynamic response) has typically a duration of about one hour (18), $T_2^*$-weighted imaging of the brain can be performed for about 1 h after contrast administration with only minor variations of the susceptibility contrast effect (i.e. signal loss) due to clearance of the agent from the blood stream. Specifically, it is necessary to be in a position to measure signal loss in brain tissue caused by neuronal activation distinctly from any variations in brain SI due to clearance of the agent from the blood stream. Thus, the baseline SI in absence of diagnostic challenge must either be flat or it may display a drift which can easily be corrected for by mathematical treatment of the data.

In an especially preferred embodiment, susceptibility contrast agents are considered with plasmakinetics allowing for a time window of 2 h during which plasma clearance, assessed as $\{R_2^*(t_2)-R_2^*(t_1)\}/R_2^*(t_1)$ where $t_1$ and $t_2$ are any two time points after i.v. administration with $t_2=t_1+2$ h, is inferior to the value of 0.4, preferably inferior to 0.3. Such extended plasma half life may, for example, be achieved by having magnetic crystals coated with, mixed to or bound to suitable materials which provide anti-opsonizing properties and in general enhanced resistance to Reticular Endothelium System (RES) uptake. Such materials include synthetic and natural polymers like polyoligosaccharides, polyaminoacids, polyalkyleneoxides, polyethyleneglycole and heparinoids. These polymers may be substituted with negatively charged groups as for instance carbon, sulfur or phosphorous oxyacid functional groups or mixed with compounds bearing such groups, which display high affinity for the surface of the crystals of the magnetic core, usually mixtures of iron oxide crystals like magnetite and maghemite. Some specific examples of materials with anti-opsonizing properties which belong to this embodiment are described by Tournier in U.S. Pat. No. 5,464,696, U.S. Pat. No. 5,587,199, and U.S. Pat. No. 5,545,395 (mixture of glycerophosphatidic acid and ethylene oxide-propylene oxide block copolymer), by Pilgrim in U.S. Pat. No. 5,160,725 and in WO-94/21240 (methoxypolyethyleneglycole phosphate), and include 512B dextran (11 kD) as used in the case of MION as described by Weissleder (19, 6).

In a third preferred embodiment, this invention relates to the repeated measurement of rCBV at the equilibrium distribution of the described contrast agents (46, 47). The underlying assumptions are that a) monoexponential decay of the transversal magnetization which therefore can be described by monoexponential time constants $T_2$ and $T_2^*$ (or their inverse values, the relaxation rates $R_2$ and $R_2^*$) and that (b) the change in $\Delta R_2^*$ following contrast agent administration is a function of the concentration f(c) and proportional to the blood volume V, $$\Delta R_2^* = k'f(c)V \qquad (eq\ 1)$$

$$\Delta R_2^* = k\ V \qquad (eq\ 1a)$$

so that in case of constant concentration of the agent in blood (eq 1) simply states a proportionality between $\Delta R_2^*$ and the blood volume in the region of interest (eq 1a). Under assumption a) SI in $T_2^*$-weighted images can be computed as $$S = K\ exp(-TE\ R_2^*) \qquad (eq\ 2)$$

where all $T_1$ and proton density effects are lumped together in the constant k.

Assessment of changes in rCBV is carried out by measuring three different SI of brain tissue, namely $S_{pre}$, i.e. the SI prior to contrast administration, $S_b$, i.e. the baseline SI after contrast and at rest, and $S_c$, i.e. the SI after contrast administration and after administration of a stress or therapeutic agent providing the diagnostic challenge. If $R_2^*$ pre is the transversal relaxation rate of the native brain tissue, $V_0$ is the value for rCBV at rest, and $\Delta V$ is the change in rCBV induced by diagnostic stress, the SI indicated above can be computed as $$S_{pre} = K\ exp(-TE\ R_{2\ pre}^*) \qquad (eq\ 3)$$

$$S_b = K\ exp(-TE\ R_{2\ pre}^*)exp(-TE\ kV_0) \qquad (eq\ 4)$$

$$S_c = K\ exp(-TE\ R_{2\ pre}^*)exp(-TE\ kV_0)exp(-TE\ k\Delta V) \qquad (eq\ 5)$$

and rCBV changes can be quantified as $$\Delta V/V_0 = \{ln\ S_c/S_b\}/ln(S_b/S_{pre}). \qquad (eq\ 6)$$

Measurements are preferably carried out in a way that maximizes the Contrast-to-Noise-Ratio (CNR), defined as the signal change during pharmacological or functional challenge divided by the noise. For a given change in rCBV and for a given contrast agent, the CNR will depend on the Echo Time (TE) of the MRI sequence and on the concentration of the agent in blood (and therefore on the administered dose). Longer echo times will increase the signal change during challenge but will also increase the noise in baseline postcontrast scans. The same effects are obtained increasing the concentration of the contrast agent. The optimum signal drop from precontrast to baseline postcontrast scans can be computed taking into account the following formula for the CNR, which is based on the definition given above:

$$CNR = S_{pre}exp(-TE\ k\ V_0)\{exp(-TE\ k\Delta V)-1\} \qquad (eq\ 7)$$

where the term in parenthesis represents the fractional signal change upon stimulation, and the term outside parenthesis represents the signal-to-noise-ratio in the postcontrast baseline scan.

If (eq 7) is maximized with respect to k, we find that for values of $\Delta V$ around 0.2 $V_0$, i.e. for fractional rCBV changes of around 20% as they are likely to occur during phMRI experiments, the highest CNR is achieved when the condition $$TE\ k\ V_0 = 1 \qquad (eq\ 8)$$

is met. According to (eq 1), this is equivalent to the condition $$TE\Delta R_2^*(0) = 1 \qquad (eq\ 8a)$$

$\Delta R_2^*(0)$ being the change in transverse relaxation rate occurring upon administration of the contrast agent. In other words, the optimal signal drop after contrast is achieved, for any given contrast agent and for any given concentration of the agent in blood, when TE is approximately equal to the change in $T_2^*$ observed following contrast administration. According to (eq 3) and (eq 4), this means that $S_b = S_{pre} \cdot e^{-1}$. Thus the optimal signal drop between precontrast and baseline postcontrast scans amounts to $S_{pre}(1-e^{-1})$, or roughly 60% of the precontrast SI. This can be achieved by an infinite combination of TE values and contrast agent doses, obviously depending on the possibly administrable dose. In practice, it is preferable to achieve the highest $\Delta R_2^*(0)$ values compatible with the tolerability and magnetic susceptibility of the contrast agent, and to adjust TE to meet the condition of eq 8a).

Animal experiments described in the examples below show that $\Delta R_2^*$ values between 10 and 30 $s^{-1}$ can readily be achieved at 2T, and that good results (substantial increase on CNR over the BOLD effect) can be achieved with TE values ranging between 0.25 $\Delta R_2^*$ and 2$\Delta R_2^*$.

As for the other MRI parameters, the present invention can be implemented using a wide range of MRI sequences. Gradient echo sequences like FLASH or SPGR or similar may be used (20) with TE set to match $\Delta R_2^*$ as described above, and with repetition time (TR) set to allow for significant relaxation of brain tissue between successive phase-encoding steps (for instance TR=500 ms at 2T), and with the flip angle ($\alpha$) set to satisfy the Ernst condition (21, 22). Echoplanar Imaging (EPI) may also be used but it is not a must due to the high sensitivity of the experiment which makes it less vulnerable to patient motion during scans. Gradient-Echo Echoplanar imaging (GE-EPI) may be used, again with TE set to match $\Delta R_2^*$ as described above and TR long enough to allow for sufficient relaxation. Spin Echo (SE) sequences both of the traditional (spin-warp) or of echoplanar (SE-EPI) type may also be used adjusting TR and TE as described above, but taking into account that in the case of SE sequences TE must be set to match $\Delta R_2$ rather than $\Delta R_2^*$, thereby resulting in shorter echo times and higher contrast agent doses.

In a fourth, particularly preferred embodiment our invention deals with detection, diagnosis and guidance of therapy for neurological, neurodegenerative, and psychiatric diseases as for instance, but not limited to, Parkinson's disease (PD), Alzheimer's disease (AD), Huntington's chorea, and schizoplhrenia. In PD, for instance, loss of dopaminergic neurons is known to progress for a long period of time before clinical symptoms are observed, often only after 70% of the dopaminergic innervation has been lost (23, 24, 25). By measuring quantitatively the hemodynamic response, more precisely the rCBV change following administration of a dopamine release agonist, as, for instance, amphetamine, one can probe the dopaminergic system, assess the severity of the disease, and identify early on persons at risk. The feasibility of such an approach is demonstrated in the examples below by showing the hemodynamic response to activation by amphetamine in a normal rat brain.

Therapeutic approaches to PD usually involve administration of L-DOPA, the precursor of the neurotransmitter Dopamine (DA), sometimes combined with substances like carbidopa which block the peripheral conversion of L-DOPA to DA thus enhancing the availability of L-DOPA for the CNS. Although L,-DOPA replacement therapy has proven to be very efficacious, it is difficult to optimize the dosage. Too high dosing may lead in the short term to dyskinesia, while in the long term it may even accelerate the degradation and loss of DA neurons (26). Optimization of the dose by neuropsychological tests alone is a time-consuming and perhaps even dangerous approach. On the contrary, our invention may be used to measure objectively, quantitatively and with high spatial resolution the response of the dopaminergic system to L-DOPA administration in PD patients. The feasibility of this application is demonstrated in the examples below by measuring rCBV changes following neuronal activation by the DA agonist apomorphine in a rat model of PD. Moreover, alternative treatments involving DA agonists are available today or are under investigation. Drugs already approved by the FDA include pergolide, bromocryptine, cabegoline (which claims a longer duration of action) which have recently been joined by promipexole and ropinirole. It is certain that individual patients will show a different response to the various drugs, and it may be practically impossible to determine the optimal treatment for each patient by neuropsychological tests only.

The present invention offers a quantitative, objective and efficient way to compare the efficacy of various drugs in the treatment of PD. It can equally well be applied to diagnosis, staging and guidance of therapy of Alzheimer's disease which affects four million people in the US alone. As already mentioned, successful application of PET is hampered by the high cost and the requirements for cyclotron and technical support. Measurements of rCBF by SPECT, on the other hand, have been found to be "of limited application for identifying mildly demented AD patients, . . . and of limited value for distinguishing moderately to severely demented patients with AD or vascular dementia" (27). Although success of therapeutic treatments of AD is, at present, still limited, early diagnosis is nevertheless important (a) in order to rule out other causes like tumors or stroke which might be treated successfully and (b) because the few therapeutic agents known today work best in the early stages of the disease.

Up to now, the most promising therapeutic approaches to AD have been developed following the hypothesis of a central role of the cholinergic system in AD. This hypothesis is corroborated by the role of cholinergic transmission in modulating learning and memory (28), by postmortem studies linking cholinergic abnormalities to the degree of cognitive impairment (29, 30), and by the decline in acetylcholine levels observed in AD patients. It is therefore not surprising that some of the most promising therapeutic agents are inhibitors of the acetylcholinesterase, which breaks down the neurotransmitter acetylcholine (AC) in normal metabolism, or AC agonists. In this case our method can greatly facilitate the critical task to find the best dose without having to rely solely on neuropsychological testing.

In the case of the first drug approved by the FDA for the treatment of AD (28), the cholinesterase inhibitor THA or tetrahydroaminoacridine, optimum dose levels have been found to vary greatly between individuals. Also, our invention can facilitate comparison between the efficacy of similar drugs, as between THA and other cholinesterase inhibitors in development or already in clinical practice as, for instance, endonebenzyl or between cholinesterase inhibitors and cholinergic releasing agents like for instance DuP 996 (31) or HP 749 (32), which are in clinical and preclinical development, respectively.

The application of our method will make it easier to manag,e successfully another widespread and devastating brain disorder, i.e. schizophrenia. The central role of dopaminergic neurotransmission in the ethiology and pathophysiology of this disease is undisputed, and is consistent with the correlation between the affinity of neuroleptics for DA receptors and their clinical efficacy. Neuroleptics are DA antagonists which compete with the neurotransmitter for postsynaptic receptors, which are upregulated in schizophrenia. Thus, they interfere with dopaminergic neurotransmission and hereby alleviate many of the so-called positive symptoms of the disease like, for instance, enhanced perception of sensorial stimuli, hallucinations and delusions (33, 34). However, such antipsychotic properties are often associated with dose-dependent adverse effects, most commonly so-called extrapyramidal symptoms (EPS) like Parkinsonism and akathisia (35), which impair quality of life and patient compliance.

Very recently the pharmaceutical industry has undertaken strong efforts in developing a whole new generation of so-called atypical antipsychotics, which claim to have antipsychotic efficacy without eliciting significant EPS (36, 37, 38). Examples of therapeutic agents, some approved, some in clinical trials, include clozaril, respridol, olanzapine, sertindol, etc. Some of these drugs interfere also with other neurotransmitter systems; clozaril, for instance, is a serotonin antagonist. This development poses both a chance and a problem for patients and for the medical community. In fact, correct dosing of neuroleptics or comparison of neurleptics and atypical antipsychotics or comparison between the various atypical antipsychotics is very difficult relying only on psychopharmacological tests or existing imaging tests. Again, application of our invention would result in a quick and quantitative assessment of efficacy, thus giving a satisfactory response to the above disclosed medical need.

EXAMPLE 1

Superparamagnetic Blood Pool Agent

Superparamagnetic blood pool agents were prepared according to the teaching of U.S. Pat. No. 5,464,696. The formulations were obtained according to the following procedures:

(a) a formulation containing iron, monosodium salt of dipalmitoylphosphatidic acid (DPPA.Na), and Synperonic F-108 in a 3/15/15 proportion, respectively, was prepared using the following procedure: 3.930 g $FeCl_3$ 6 $H_2O$ (14.54 mmol.) and 2.930 g $FeCl_2$ $4H_2O$ (14.74 mmol.) were dissolved in 250 mL of water. The mixture was stirred and ammonia 25% in aqueous solution was added dropwise until the pH reached a stable value of 9.0. The suspension of black particles formed was heated for 5 min at 75° C. and the particles were allowed to precipitate and settle at room temperature. The precipitate was washed two times by decantation with portions of 500 mL of Tris (1 g/L) glycerol (0.3 M) solution. After washing, the particles were again suspended in 500 mL, Tris-glycerol buffer pH 7.25 under agitation. The iron concentration in the suspension was 3.01 mg/mL. To 300 mL of this suspension 4500 mg of DPPA.Na and 4500 mg of Synperonic F-108 (from ICI) were added. Sonification was effected for 20 min (BRANSON 250 Sonifier, output 60). The temperature which rose to 84° C. during sonication was allowed to drop to room temperature. The suspension of the coated iron oxide particles was filtered on 0.45 $\mu$m membrane and stored in 20 mL sterile bottles. Measurement by means of a Coulter nanosizer apparatus indicated that the average particle size was 79 nm. Measurement by means of a Johnson Matthey Magnetic Susceptibility Balance indicated that the mass magnetic susceptibility of the sample was equal to $43,663 \times 10^{-6}$ cgs.

(b) a formulation containing iron, DPPA.Na, and Synperonic F-108 in a 3/30/30 proportion, respectively, was prepared using the procedure described in example 1a) with the exception that 9000 mg of DPPA.Na and Synperonic F-108 were respectively used instead of 4500 mg.

EXAMPLE 2

Baseline Signal Loss in Normal Rat Brain

The superparamagnetic blood pool contrast agent prepared as described in example 1a) was administered intravenously to three normal Sprague-Dawley (SD) rats at a dose of 60 $\mu$mol Fe/kg (1 mL/kg). MR images were taken on a 2T SMIS animal research imager using a dedicated 4 cm i.d. birdcage Radio Frequency (RF) coil and a Gradient Echo 500 ms/30 ms/30° (TR/TE/$\alpha$) sequence. Images were taken prior to and at various time points after contrast. Initial signal loss of brain tissue, measured at 5 min after administration, amounted to 46% of the precontrast SI. After 2 h, signal loss amounted still to 32% of precontrast, or to 70% of the initial effect. The SI time course of this set of experiments is represented in FIG. 1. By using the formula $\ln\{S_{pre}/S_b\}/TE=\Delta R_2^*$ where Spre and Sb mean precontrast and postcontrast baseline SI, respectively, the initial increase in the transversal relaxation rate, $\Delta R_2^*$, was assessed to be equal to 20.5 $s^{-1}$.

Figure 2:
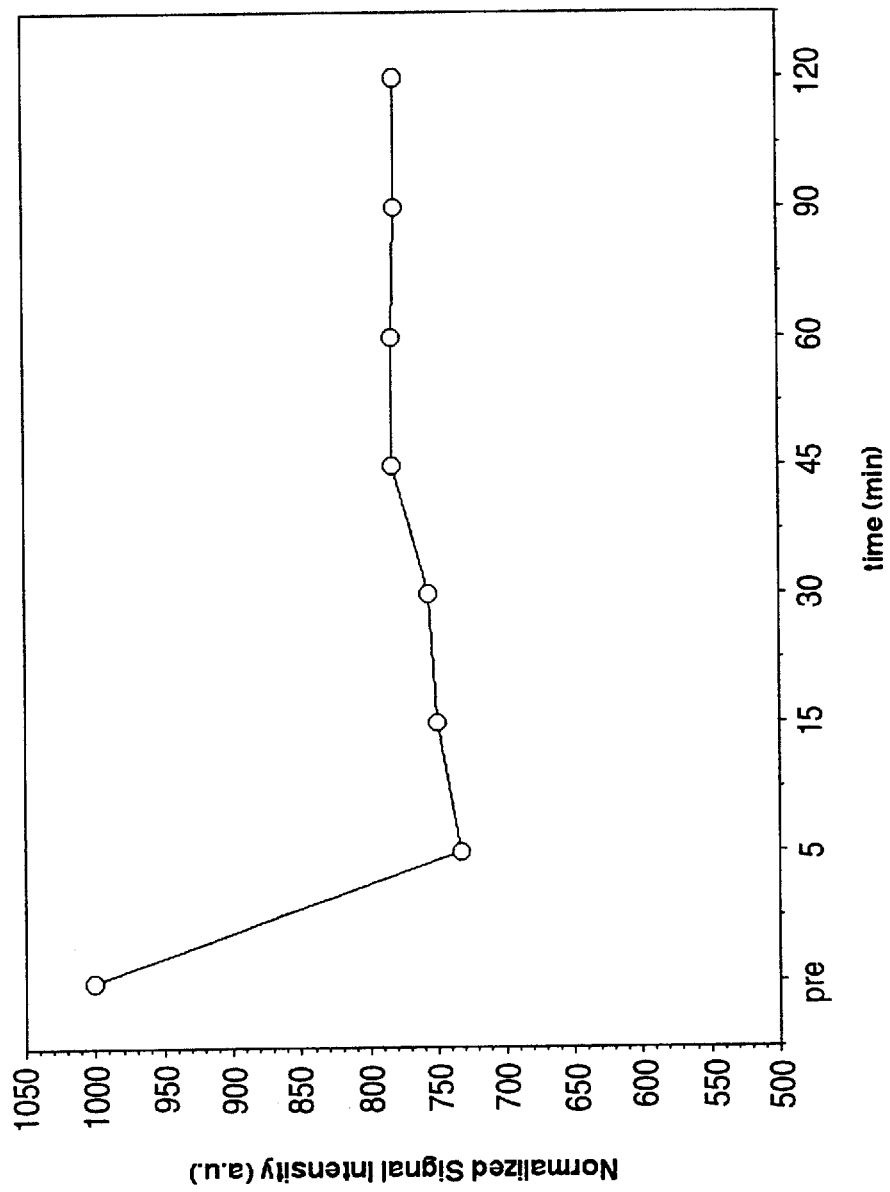
FIG. 2 is a normalized signal intensity time curve of rat brain after 60 μmol Fe/kg of the superparamagnetic contrast agent described in example 1b), at 2T using Spin-Echo Echo Planar Imaging sequence (1000 ms/70 ms; TR/TE).

In a further series of experiments, the contrast agent prepared as described in example 1b) was administered i.v. at the dose of 40 $\mu$mol/kg to four normal SD rats which were subjected to MRI at 2T prior to and up to 2 h after administration using a SE-EPI 1000 ms/70 ms (TR/TE) sequence. Initial signal loss was found to be equal to 26.7%, corresponding to an increase in the transversal relaxation rate $\Delta R_2$ of 4.46 $s^{-1}$, decreasing to the value of 3.56 $s^{-1}$ at 2 h after contrast administration as shown in FIG. 2.

In a further set of experiments, a Monocrystalline Iron Oxide Nanocolloid (MION) as described by Mandeville (7) was administered intravenously to three normal SD rats at a dose of 180 $\mu$mol of Fe/kg. At 2T and using a 1000 ms/50 ms (TR/TE) SE-EPI sequence, an initial increase of 6.0 $s^{-1}$ in the transversal relaxation rate $\Delta R_2$ was observed in brain tissue (corresponding to a signal loss of 26% at an echo time TE of 50 ms), which remained unchanged over the period of observation of 2 h.

EXAMPLE 3

Comparison of phMRI Experiments in Control Animals Using the BOLD Effect and Superparamagnetic Blood Pool Agents Two groups of three normal SD rats each were imaged to assess the rCBV changes associated with pharmacological stimulation by amphetamine, a dopamine release agonist which is known to increase the extracellular concentration of DA in the brain, probably by activation of the DA transporter receptor (45). All the animals were imaged at 4.7T in a Bruker animal research imager using a gradient echo 500 ms/20 ms (TR/TE) sequence with the excitation angle alpha set to satisfy the Ernst condition.

Figure 3:
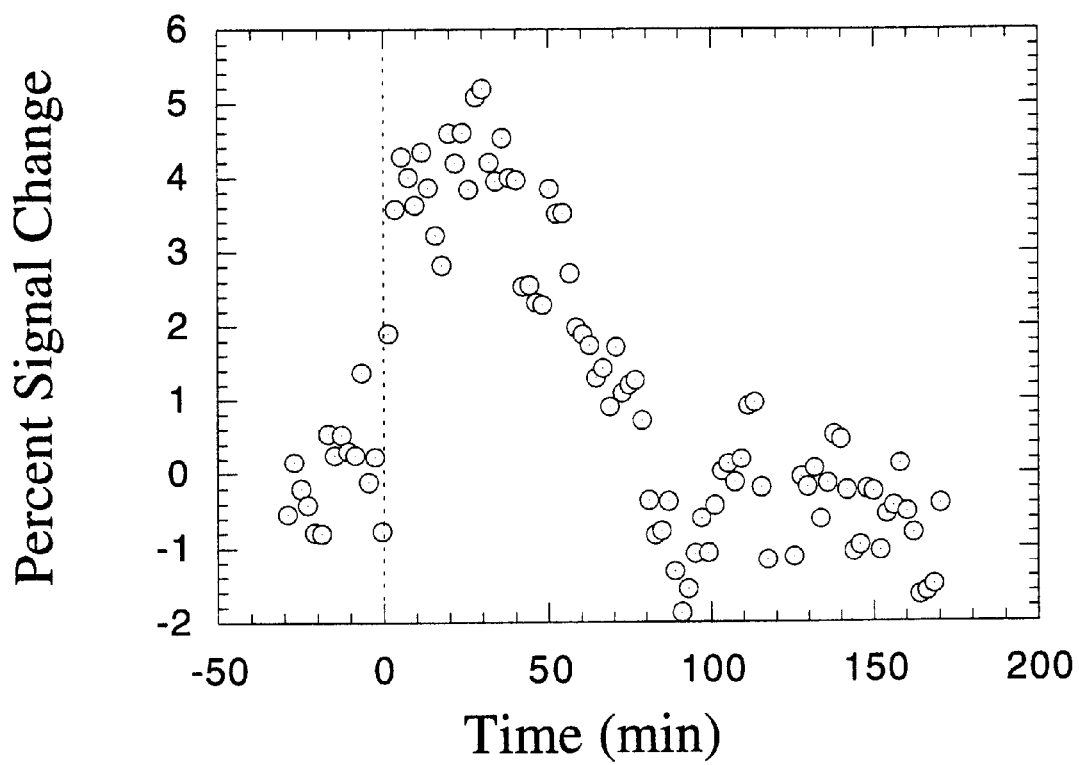
FIG. 3 is a scattergram showing the percent signal change time course of rat brain after 3 mg/kg amphetamine activation using BOLD effect at 4.7T.

One group of rats was imaged using the BOLD technique as described by Chen et al. (18). After having obtained a stable baseline for at least 12 acquisitions, stimulation was performed by i.v. administration of 3 mg/kg of amphetamine, and further images were then acquired for 3 h at 5 min intervals. All three animals showed activation in areas of the brain known to have the highest dopaminergic innervation, i.e. in the frontal cortex and in the striatum. Signal intensity loss in the frontal cortex peaked at 30–40 min after stimulation at a value of about 5% below baseline and in all cases was back to zero after 100 min as shown in FIG. 3. Activation maps were computed using Komolgorov-Smirnov statistics (39) and fused with the original MR images as shown on the top of FIG. 4. Different colors are used to represent different values of the parameter p, which describes the statistical significance of any change in SI observed relative to baseline after activation. Note the relatively poor definition of the activating area, and that the yellow color codes are for a p value of $10^{-8}$.

Figure 4:
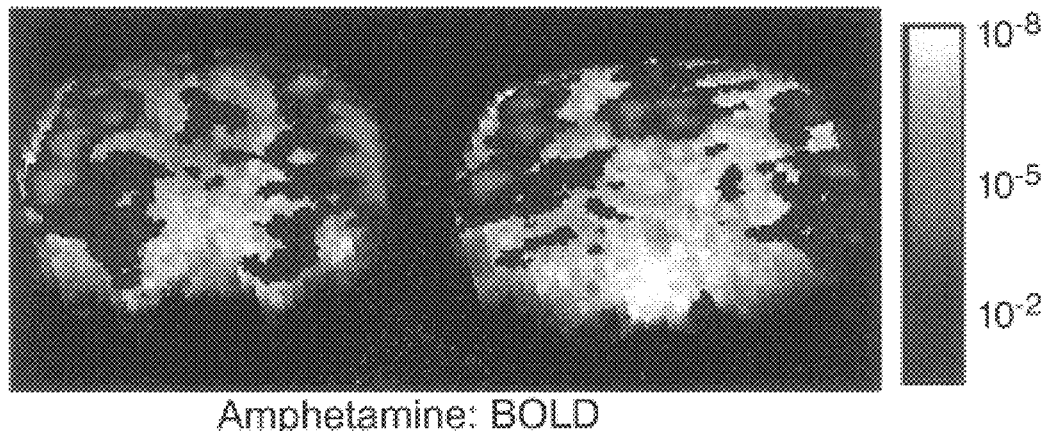
FIG. 4 is a comparison of activation maps obtained after stimulation with 3 mg/kg i.v. of amphetamine using the BOLD effect (FIG. 4A) and after contrast (60 μmol Fe/kg i.v. of the superparamagnetic contrast agent described in example 1b) (FIG. 4B). Yellow in the color bar indicates a p value of <$10^{-8}$ for the BOLD and $10^{-19}$ for the contrast agent measured using Komolgorov-Smirnov statistics. Both data sets were collected at 4.7T using a gradient echo sequence.
Figure 4:
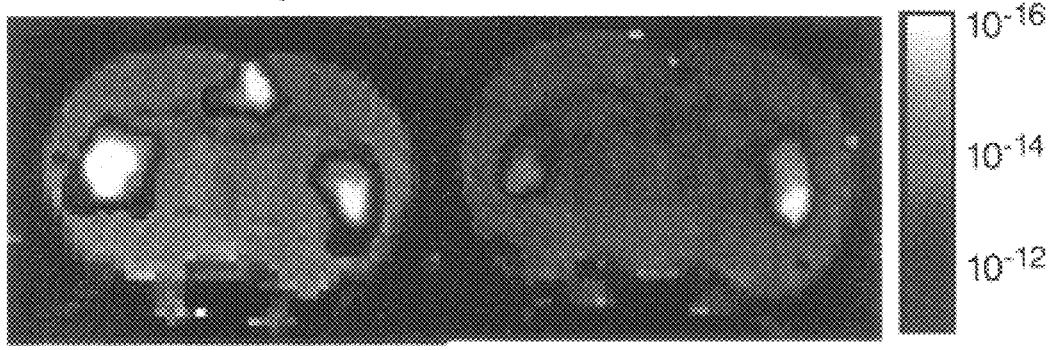
Figure 5:
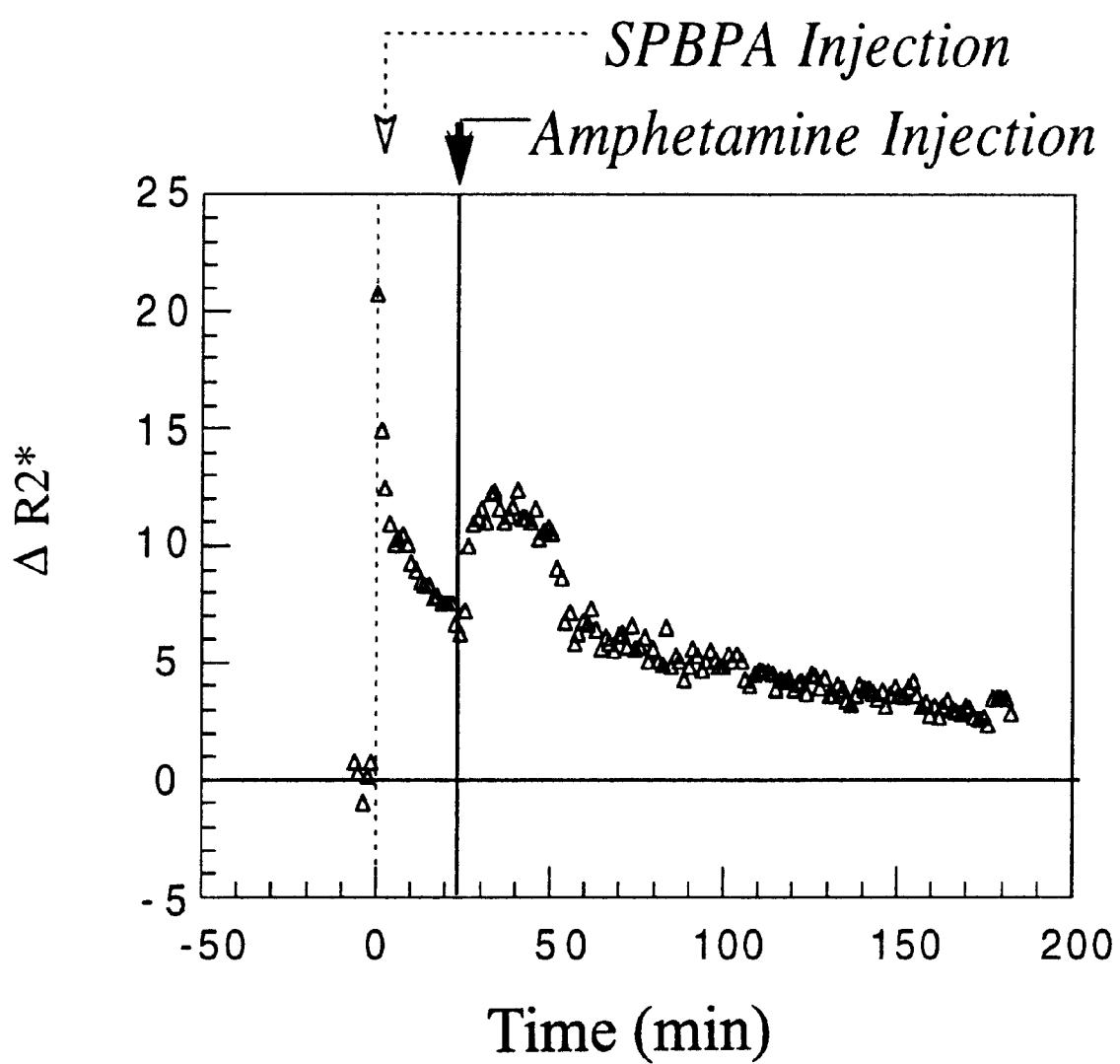
FIG. 5 is a graph showing the $\Delta R_2^*$ time course of a rat brain activated with 3 mg/kg i.v. of amphetamine, administration of 60 μmol Fe/kg of the superparamagnetic contrast agent described in example 1b).

Animals the other group were subjected to MR imaging using the same MR parameters, and received a dose of 60 $\mu$mol/kg (1 mL/kg) of the contrast agent described in example 1b). Fifteen minutes after contrast administration, stimulation was induced as for the animals in group one, and images were taken up to 3 h after contrast. The time course of $\Delta R_2^*$ is represented in FIG. 5. Following stimulation, there is an increase of 6 $s^{-1}$ in $\Delta R_2^*$ (the corresponding for the BOLD experiment is 2.4 $s^{-1}$), which translates in a signal loss of 10%. The drift in the baseline could easily be corrected for by linear extrapolation. The activation maps obtained from one of the animals in the group receiving contrast are shown in the bottom of FIG. 4. The spatial resolution and the statistical significance of activation obtained in this group are much higher than those achieved with the BOLD effect. Note that the yellow color in the map obtained after contrast codes for a p value of $10^{-16}$ compared to a value of $10^{-8}$ in the map obtained with the BOLD effect.

EXAMPLE 4

Comparison of phMRI using BOLD with phMRI using susceptibility contrast agents with extended plasma half life in animal models of Parkinson's Disease Eight normal SD rats were subjected to selective, localized depletion of striatonigral dopaminergic innervation by stereotaxic, unilateral intracerebral injection of 8 $\mu g/2$ $\mu l$ of 6-hydroxydopamine (6-OHDA), a DA analogue which is uptaken by the DA transmitter receptor, subsequently concentrating in the neurons causing their degeneration (40). Intracerebral administration of 6-OHDA is a well described (41, 42, 43) model of PD. One of the symptoms associated with 6-OHDA lesion is rotational preference, meaning that lesioned animals prefer ipsiversive over contraversive turns, a pattern observed also in humans which preferentially rotate toward the side where the brain hemisphere is relatively hypodopaminergic (44). After lesioning, animals were allowed to recover for 3 weeks, and neurological symptoms were assayed by rotational testing in a computerized rotameter (San Diego Instruments, CA). Six animals showed more than 600 ipsilateral turns per 90 min interval and were admitted to the study, since such a behavior is indicative of a loss of at least 90% of striatonigral dopaminergic innervation (41). The animals were divided in two groups of three rats each.

All animals were subjected to MRI at 4.7T using the same MRI equipment and sequence as described in Example 3. For animals in group one, pharmacological stimulation was performed by i.p. administration of 5 mg/kg of apomorphine after acquisition of twelve stable precontrast images. Further images were then taken for 3 h at 5 min intervals. Animals in group two received intravenously 57 $\mu mol/kg$ of the contrast agent described in Example 1a) after acquisition of 12 stable precontrast images. Postcontrast baseline images were taken up to 30 min after contrast. A this time point, stimulation was carried out as for rats in group one, followed by imaging at 5 min intervals up to 3 h after contrast.

Figure 6A:
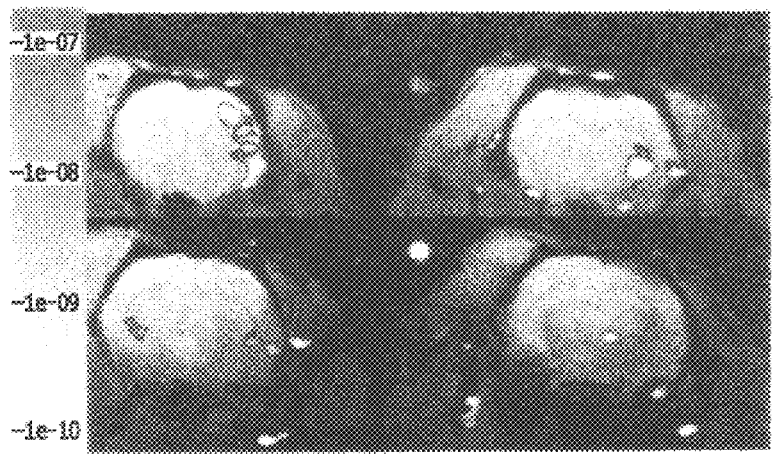
FIG. 6 is an activation map (FIG. 6A) and $\Delta R_2^*$ time course (FIG. 6B) of the signal increase on the ipsilateral side in a rat model of Parkinson's disease after i.v. administration of the superparamagnetic contrast agent described in example 1a) at the dose of 57 μmol Fe/kg. The rat has been lesioned on the right side with 6-hydroxydopamine (6-OHDA). There is a pronounced increase in the blood volume on the ipsilateral side after injection with apomorphine. There is no response on the contralateral side due to the presence of normal levels of dopaimine in the striatum. This represents evidence of super-sensitivity (upregulation of post-synaptic dopamine receptors after lesioning of the ipsilateral side) a well known effect in 6-hydroxydopamine lesioned animals. The present invention offers the possibility to quantify this effect in, for instance, patients with Parkinson's disease.
Figure 6B:
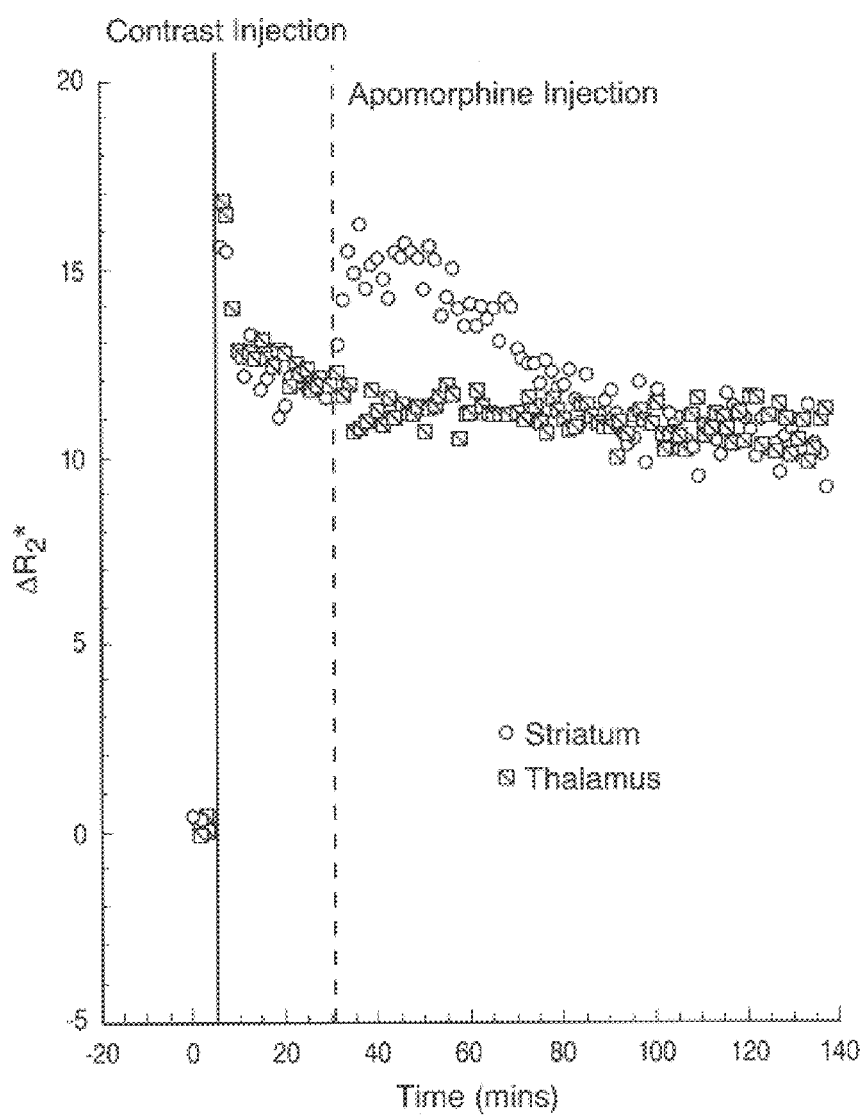

Activation maps, computed using the methodology described in Example 3 from images taken after contrast and fused with precontrast GRE images, are shown in FIG. 6 for various brain slices of a rat lesioned on the right side. An increase in rCBV can be detected in the lesioned area, but not contralaterally. This is an evidence of upregulation of DA receptors in the lesioned area, and is consistent with the notion that modest increases in extracellular DA concentration, as elicited by apomorphine at the dose used in our experiments, lead to neuronal activation in the areas depleted of dopamine, but not in areas with normal DA concentration. Upregulation of postsynaptic DA is said to play a critical role in both PD and schizophrenia. The time course of $\Delta R_2^*$ for animals of group 2 is also shown in FIG. 6. No activation could be detected in animals of group one.

EXAMPLE 5

A normal Sprague-Dawley rat was lesioned unilaterally with 6-OHDA as described in Example 4), was allowed to recover for 3 weeks, and was found to test positively for ipsiversive rotational preference. Stimulation with 4 mg/kg i.p. of amphetamine was carried out 15 min after administration of contrast as described in Examples 3) and 4). Ninety min after receiving amphetamine, the animal was stimulated with 5 mg/kg i.p. of apomorphine.

Figure 7:
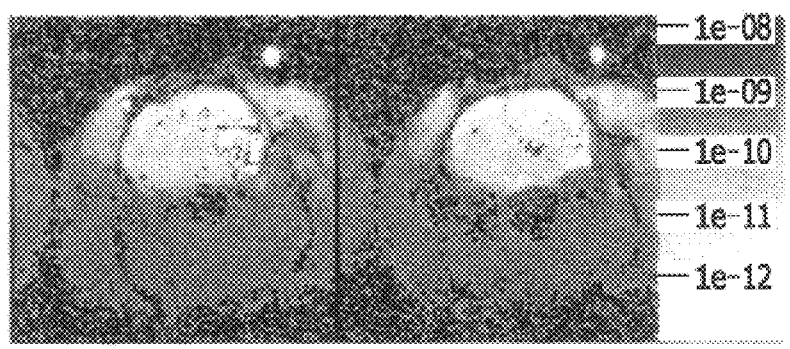
FIG. 7 is an activation map of a unilaterally (left hemisphere) 6-OHDA lesioned rat taken 10 min after stimulation with amphetamine. Note that activation is seen on the contralateral hemisphere only.
Figure 8:
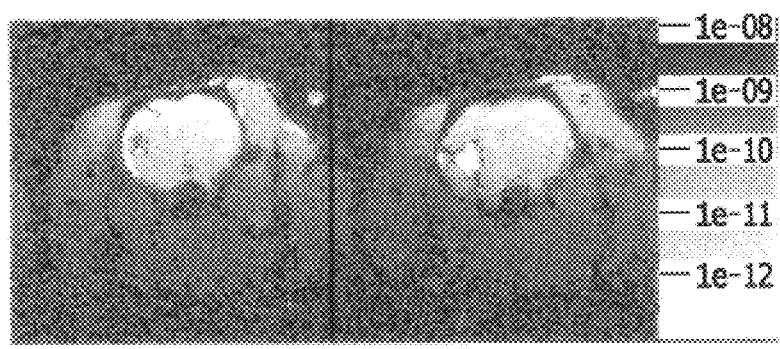
FIG. 8 is an activation map taken for the same animal as in FIG. 7, ten min after stimulation with apomorphine. Note that activation is seen on the ipsilateral hemisphere only.

MRI was performed prior and after contrast using the equipment and the sequences described in Examples 3) and 4), and activation maps after amphetamine and after apomorphine were computed, again using the techniques described in examples 3) and 4). Both activation maps are displayed in FIG. 7 and FIG. 8. In the map taken after amphetamine stimulation, only the hemisphere contralateral to the lesion, on the right side in FIG. 7, shows activation. On the contrary, in the map taken after apomorphine stimulation, only the hemisphere ipsilateral to the lesion shows activation (on the left side in FIG. 8). This example provides evidence that the method of the present invention can be used to detect and quantitate both depletion and supersensitivity of dopaminergic innervation.

REFERENCES

1. Marota J., Mandeville J B., Ayata C., Kosovsky B., Weissleder R., Hyman S., Moskowitz M., Weisskoff R M., Rosen B R. Activation of Rat Brain by Cocaine: Functional Imaging with BOLD and Cerebral Blood Volume. In: Proceedings of the ISMRM Fifth Scientific Meeting and Exhibition, Vancouver, B.C., Canada, Apr. 12–18, 1997:731.
2. Huber J., Soliman K F A. Prenatal Cocaine Exposure Altered the Response to Stress, NMDA Administration and Pain in the Rat. In: Proceedings of the Society of Neuroscience, 1997;23: 105.17.
3. Berry I., Benderbous S., Ranjeva J P., Garcia-Meavilla., Manelfe C., & Le Bihan D. Contribution of Sinerem Used as Blood-Pool Contrast Agent: Detection of Cerebral Blood Volume Changes during Apnea in Rabbit. MRM, 1996;36:415–419.
4. Bush C H., Mladinich C R., Montgomery W J. Evaluation of an Ultrasmall Superparamagnetic Iron Oxide in MRI in a Bone Tumor Model in Rabbits. J Magn Reson Imaging, 1997;7(3):579–584.
5. Harisinghani M G., Saini S., Slater G J., Sclnall M D., Rifkin M D. MR Imaging of Pelvic Lymph Nodes in Primary Pelvic Carcinoma with Ultrasmall Superparamagnetic Iron Oxide (Combidex): preliminary observations. J Magn Reson Imaging, 1997;7(1):161–163.
6. Shen T., Weissleder M., Papisov J., Bogdanov A., Brady T J. Monocrystalline Iron Oxide Nanocompounds (MION): Physiochemical Properties. Magn Reson. Med., 1993;29:599–604.
7. Mandeville J., Moore J., Chesler D., Garrido L., Weissleder R., Weisskoff. Dynamic Liver Imaging with Iron Oxide Agents: Effects of Size and Biodistribution on Contrast. Magn. Reson. Med., 1997;37:885–890.
8. Schaffer B K., Linker C., Papisov M., Tsai E., Nossiff N., Shibata T., Bogdanov J A., Brady T J., Weissleder R. MION-ASF: Biokinetics of an MR Receptor Agent. Magn. Reson. Imag. 1993;11:411–417.
9. Jung C W., Weissleder R., Josephson L., Bengele H., Brady T J. Physical Properties of MION-46 and AMI-227. In:Proc., Int.Soc.Magn.Reson.Med, 4th Annual Meeting, New York, N.Y., 1996:1681.
10. Majumdar S., Zoghbi S S., Gore J C. Pharmacokinetics of Superparamagnetic Iron-Oxide MR Contrast Agents in the Rat. Investigative Radiology, 1990;25:771–777.
11. Weissleder R., Stark D D., Engelstad B L., Bacon B R., Compton C C., White D L., Jacobs P., Lewis J. Superparamagnetic Iron Oxide: Pharmacokinetics and Toxicity. American Journal of Roentgenology, 1989;152:167–173.

12. Schwartz L H., Seltzer S E., Adams D F., Tempany C M C., Piwnica-Worma D R, Silverman S G., Herman L., Hlerman L T., Hooshmand R. Effects of Superparamagnetic Iron Oxide (AMI-25) on Liver and Spleen Imaging Using Spin-Echo and Fast SpinEcho Magnetic Resonance Pulse Sequences. Investigative Radiology, 1994;29:S21–S23.

13. Kent T A., Quast M J., Kaplan B J., Lifsey R S., Eisemberg I I M. Assessment of a Superparamagnetic Iron Oxide (AMI-25) as a Brain Contrast Agent. Magn Reson Med, 1990;13 :434–443.

14. Reimer P., Schuierer G., Balzer T., Peters P E. Application of a Superparamagnetic Iron Oxide (Resovist) for MR Imaging of Human Cerebral Blood Volume. MRM, 1995;34:694–697.

15. Hamm B., Staks T., Taupitz M. A New Superparamagnetic Iron Oxide Contrast Agent for Magnetic Resonance Imaging. Invest Radiol, 1994;29:S87–S89.

16. Vogl T J., Hammerstingl R., Schwarz W., et al. Magnetic Resonance Imaging of Focal Liver Lesions. Comparison of the Superparamagnetic Iron Oxide Resovist versus Gadolinium-DTPA in the Same Patient. Invest Radiol, 1996;31(11):696–708.

17. Kopp A F., Laniado M., Dammann F., et al. MR Imaging of the Liver with Resovist: safety, efficacy, and pharmacodynamic properties. Radiology, 1997;204(3):749–756.

18. Chen Y C I., Galpern W R., Brownell A L., Matthews R T., Bogdanov M., Isacson O., Keltner J R., Beal M F., Rosen B R., Jenkins. Detection of Dopaminergic Neurotransmitter Activity Using Pharmacological MRI: Correlation with PET, Microdialysis, and Behavioral Data. MRM, 1997;38:389–398.

19. Weissieder R., Elizondo G., Wittenberg K. Ultrasmall Superparamagnetic Iron Oxide. Characterization of a New Class of Contrast Agents for MR Imaging. Radiology, 1990;175:489–493.

20. Wehrli F W. Fast-Scan Magnetic Resonance, Principles and Applications, 1991, Raven Press, Ltd., NY, N.Y.

21. Ernst R R., Anderson W A. Application of Fourier Transform Spectroscopy to Magnetic Resonance. Rev Sci Inst, 1966;37:93–102.

22. Mills T C., Ortendahl D A., Hylton N M., et al. Partial Flip Angle MR Imaging. Radiology, 1987;162:531–539.

23. Hornykiewicz O. Neurochemical pathology and the etiology of Parkinson's disease: basic facts and hypothetical possibilities. Mt Sinai J Med, 1988;55:11–20.

24. Paulus W., Jellinger K. The neuropathological basis of different clinical subgroups of Parkinson's disease. J Neuropathol Exp Neurol, 1991;50:743–755.

25. Scherman D., Desnos C., Darchem F., Pollack P., Javoy-Agid F., Agid Y. Striatal dopamine deficiency in Parkinson's disease: role of aging. Ann Neurol, 1989;26:551–557.

26. Diamond S G., Markham C H., Hoehn M M., McDowell F H., Muenter M D. Multicenter study of Parkinson mortality with early versus later dopa treatment. Ann Neurol, 1987;22:8–12.

27. Rapoport SI. Anatomic and Functional Brain Imaging in Alzheimer's Disease. In: Psychopharmacology: The Fourth Generation of Progress, F. E. Bloom and D. J. Kupfer, eds., Raven Press, Ltd. N.Y. N.Y., 1995:1401–1415.

28. Marin D B., Davis K L. Experimental Therapeutics. In: Psychopharmacology: The Fourth Generation of Progress, F. E. Bloom and D. J. Kupfer, eds., Raven Press, Ltd. N.Y. N.Y., 1995:1417–1426.

29. Olton D S., Wenk G L. Dementia: animal models of the cognitive impairments produced by degeneration of the basal forebrain cholinergicsystem. In: Psychopharmacology: The Third Generation of Progress, Meltzer H Y, ed., Raven Press, Ltd. N.Y. N.Y., 1987:941–953.

30. Perry E K., Tomlinson B E., Blessed G., et al. Correlation of Cholinergic Abnormalities with Senile Plaques and Mental Test Scores in Senile Dementia. Br Med J, 1978;2:1457–1459.

31. Saletu B., Darragh A., Salmon P., et al. EEG Brain Mapping in Evaluating the Time Course of the Central Action of DuP 996: a New Acetylcholine Release Drug. Br J Pharmacol, 1989;28:1–16.

32. Cornfeldt M., Wirtz-Burgger, Szewczak M., Blitzer R., Hroutunian V., Effland R C., Klein J T., Smith C. Abstr Soc Neurosci, 1990;16:612.

33. Creese I., Burt D R., Snyder S H. DA Receptor Binding Predicts Clinical and Pharmacological Potencies of Antischizophrenic Drugs. Science, 1976;192:481–483.

34. Davis K L., Kahn R S., Ko G., et al. Dopamine in Schizophrenia. Am J Psychiatry, 1991 ;148: 1474–1486.

35. Van Putten T. Wliy do Schizophrenic Patients Refuse To Take Their Drugs? Arch Gen Psychiatry, 1974;3 1:67–72.

36. Borison R L., Diamond B I., Pathiragja A., Meibach R C. Clinical Overview of Risperidone. In: Meltzer M Y, ed. Novel Atypical Antipsychotic Drugs. New York: Raven Press, 1992:223–239.

37. Chouinard G., Jones B., Remington G., et al. A Canadian Multicenter Placebo-Controlled Study of Fixed Doses of Risperidone and Haloperidol in the Treatment of Chronic Schizoplrenic Patients. J Clin Psychopharmacol, 1993;13:35–40.

38. Baldessarini R., Frankenburg F R. Clozapine: A Novel Antipsychotic Agent. New Engl J Med, 1991:324:746–754.

39. Zar J H., Biostatistical Analysis, Prentice Hall Inc., Englewood Cliffs N.J., USA 1984: p.53.

40. Korczyn A D. Parkinson's Disease. In: Psyclhoplharmacology: The Fourth Generation of Progress, F. E. Bloom and D. J. Kupfer, eds., Raven Press, Ltd. N.Y. N.Y., 1995:1479–1484.

41. Perese D A., Ulman J., Viola J., Ewing S E., Bankiewicz K S. A 6-hydroxydopamine-induced selective parkinsonian rat model. Brain Res, 1989;494:285–293.

42. Zigmond M J., Abercrombie E D., Berger T W., Grace A A. Stricker E M. Compensations after lesions of central dopaminergic neurons: come clinical and basic applications, 1990.

43. Robbins T W., Everitt B J., Cole B J., Archer T., Mohammed A. Functional hypotheses of the coeruleocortical noradrenergic projection: a review of recent experimentation and theory. Physiol Psychol, 1985;13:127–150.

44. Sceman P. Dopamine Receptors, clinical correlates. In: Psychopharmacology: The Fourth Generation of Progress, F. E. Bloom and D. J. Kupfer, eds., Raven Press, Ltd. N.Y. N.Y., 1995:300.

45. Giros B., Jaber M., Jones S R., Wightman R M., Caron M G. Hyperlocomotion and difference to cocaine and amphetamine in mice lacking the dopamine transporter. Nature, 1996;379:606–612.

46. Gati J S., Menon R S., Ugurbil K., Rutt B K. Experimental Determination of the BOLD Field Strength Dependence in Vessels and Tissue. MRM, 1997;38:296–302.

47. Mandeville J B., Marota J J A., Kosofsky B E., Keltner J R., Weissleder R., Rosen B R., Weisskoff R M. Dynamic Functional Imaging of Relative Cerebral Blood Volume During Rat Forepaw Stimulation. Magn.Reson.Med., 1998:in press.

What is claimed is:

1. A method for magnetic resonance imaging (MRI) of changes in neurotransmitter and neuroreceptor activity as a metabolic response to diagnostic challenge or therapeutic treatment in a patient with suspected or already diagnosed mental illnesses of psychiatric, neurodegenerative or neurological nature, comprising the steps of:
    (a) administering to said patient a drug eliciticiting an MRI detectable hemodynamic response;
    (b) administering to said patient an MRI ferromagnetic, antiferromagnetic or superparamagnetic contrast agent with high magnetic susceptibility and
    (c) measuring, in a spatially and temporally resolved manner, relative Cerebral Blood Volume (rCBV) changes associated to neuronal activating using $T_2$- or $T_2^*$-weighted MRI scans at the equilibrium distribution of said contrast agent.

2. A method as claimed in claim 1 in which said contrast agent has plasma half life sufficient to allow for constant or sufficiently stable concentration in blood over a period of time necessary to elicit the full amplitude of the metabolic response to a drug administered for diagnostic or therapeutic purposes.

3. A method as in claim 2 where the contrast agent has plasma kinetics allowing for a time window of 2 at least two hours (2 h) during which plasma clearance assessed as $\{R_2^*(t_2)-R_2^*(t_1)\}/R_2^*(t_1)$ where $R_2^*$ is the transversal relaxation rate and $t_1$ and $t_2$ are any two time points after administration of said drug with $t_2=t_1+2$ h amounting to less than a value of 0.4.

4. A method as in claim 2 where the contrast agent has plasma kinetics allowing for a time window of 2 at least two hours (2 h) during which plasma clearance assessed as $\{R_2(t_2)-R_2(t_1)\}/R_2(t_1)$ where $R_2$ is the transversal relaxation rate and $t_1$ and $t_2$ are any two time points after administration of said drug with $t_2=t_1+2$ h amounting to less than a value of 0.4.

5. The method of claim 1 applied to diagnosis or guidance of therapy in schizophrenia.

6. The method of claim 5 applied to the assessment of success and guidance of therapy of schizophrenia by assessing the effect of administration of neuroleptics and/or antipsychotics.

7. The method of claim 6 in which the neuroleptic or the antipsychotic agent is selected from the group consisting of haloperidol, olanzapine, respirdol, and sertindone.

8. A method as claimed in claim 6 applied to determine a co-medication to minimize adverse effects of antipsychotic drugs.

9. The method of claim 1 to detect or diagnose Alzheimer's disease.

10. The method as described in claim 9 wherein said contrast agents are used for guidance and assessment of success of therapy by assessing the effect of cholinesterase inhibitors, acetylcholine agonists or of other anti AD medications.

11. The method of claim 1 applied to detection, diagnosis and staging of Parkinson's disease.

12. The method as claimed in claim 11 applied to assessment of success and guidance of therapy of Parkinson's Disease, by comparing the effects of the administration of anti-PD drugs.

13. The method of claim 11 carried out by detecting rCBV changes associated with hyperactivity of postsynaptic dopamine receptors.

14. The method as claimed in claim 12 in which the anti PD-drug is selected from the group consisting of L-DOPA, pergolide, bromocryptine, cabegoline, promipexole and ropinirole.

15. A method for measuring or depicting in a spatially and timely resolved manner the changes in regional Cerebral blood Volume (rCBV mapping) associated with changes in neurotransmitter activity exploiting the susceptibility contrast effect, employing the compartmentalization of susceptibility contrast agents in the vasculature and of the constant or nearly constant concentration in blood over time comprising the steps of:
    (a) administering to said patient a drug eliciticiting an MRI detectable hemodynamic response;
    (b) administering to said patient an MRI ferromagnetic, antiferromagnetic or superparamagnetic contrast agent with high magnetic susceptibility and
    (c) measuring, in a spatially and temporally resolved manner, relative Cerebral Blood Volume (rCBV) changes associated to neuronal activating using $T_2$- or $T_2^*$weighted MRI scans at the equilibrium distribution of said contrast agent, and relating the changes in signal intensity (SI) in $T_{=2}^*$- or $T_2$-weighted MR images to changes of rCBV.

16. A method as claimed in claim 15 where a neuronal activation map is obtained by computing and mapping statistical parameters which represent the statistical significance of the observed changes in rCBV following administration of said drug.

17. A method for mapping rCBV changes associated with neurotransmitter activity using $T_2$- or $T_{=2}^*$-weighted sequences using a ferromagnetic, antiferromagnetic or superparamagnetic susceptibility contrast agents to determine transversal apparent relaxation rates $R_2$ and $R_2^*$, wherein $T_2$ and $T_2^*$ are monoexponential time constants and $R_2$ and $R_2^*$ are transversal relaxation rates of brain tissue, apparent relaxivity meaning the time constant for the decay of transversal magnetization obtained assuming monoexponential decay after excitation by radiofrequency, using the relation $\Delta RR_2^*=-(\ln S_t/S_0)/TE$, where $\Delta R_2^*$ is the change in relaxation rate $S_t$ is the signal intensity at time t after contrast administration, $S_0$ is the precontrast signal intensity baseline and TE is the Echo Time, and relating the approximately linear relationship between $\Delta R_2^*$ and agent concentration in tissue to determine relative changes in blood volume, as $(-V_t)/V_0=(\Delta R_2^*_{(t)}/\Delta RR_2^*_{(0)})-1$, where $V_0$ is the value for rCBV at rest and $V_t$ is the value for rCBV at time t after contrast administration.

18. A method for assessing changes in neurotransmitter and neuroreceptor activity as a metabolic response to diagnostic challenge or therapeutic treatment in a patient with suspected or already diagnosed mental illness of psychiatric, neurodegenerative or neurological nature, said method comprising the steps of
    (a) inducing neuronal activation in the patient by administering a neuronal activator eliciting a hemodynamic response,
    (b) MR Imaging said patient to assess changes in the patient's regional cerebral blood volume using a negative blood and contrast agent, and thereafter
    (c) relating to the changes to the patient's condition.

* * * * *

UNITED STATES PATENT AND TRADEMARK OFFICE
CERTIFICATE OF CORRECTION

PATENT NO.    : 6,321,105 B1
DATED         : November 20, 2001
INVENTOR(S)   : Jenkins et al.

It is certified that error appears in the above-identified patent and that said Letters Patent is hereby corrected as shown below:

<u>Title page,</u>
Item [73], should read as follows:

-- [73] Assignees:  Bracco S.p.A., Milan (IT)
                    The General Hospital, Boston (MA) --

Signed and Sealed this

Eleventh Day of February, 2003

JAMES E. ROGAN
*Director of the United States Patent and Trademark Office*